United States Patent [19]

Kierney et al.

[11] Patent Number: 4,759,374
[45] Date of Patent: Jul. 26, 1988

[54] NON-INVASIVE BLOOD FLOW MEASUREMENTS UTILIZING CARDIAC CYCLE SYNCHRONIZATION

[75] Inventors: Catherine M. P. Kierney; Gustavus H. Zimmerman, III, both of Westmont, Ill.

[73] Assignee: American Telephone and Telegraph Company and AT&T Bell Laboratories, Murray Hill, N.J.

[21] Appl. No.: 730,456

[22] Filed: May 6, 1985

[51] Int. Cl.$^4$ ............................................. A61B 10/00
[52] U.S. Cl. ................................. 128/663; 73/861.25; 364/417
[58] Field of Search ............................... 128/660–663; 73/861.25; 364/415–417

[56] References Cited

U.S. PATENT DOCUMENTS

| | | | |
|---|---|---|---|
| 4,109,647 | 8/1978 | Stern et al. | 128/2.05 |
| 4,182,173 | 1/1980 | Papadofrangakis et al. | 73/194 |
| 4,217,909 | 8/1980 | Papadofrangakis et al. | 128/663 |
| 4,257,278 | 3/1981 | Papadofrangakis et al. | 73/861.25 |
| 4,265,126 | 5/1981 | Papadofrangakis et al. | 73/861.25 |
| 4,320,765 | 3/1982 | Cathignol et al. | 128/663 |
| 4,324,258 | 4/1982 | Huebscher et al. | 128/663 |
| 4,327,739 | 5/1982 | Chmiel et al. | 128/663 |
| 4,509,526 | 4/1985 | Barnes et al. | 128/663 |
| 4,575,799 | 3/1986 | Miwa et al. | 128/660 X |

OTHER PUBLICATIONS

Brian, P. et al, "Off Line Computation of LV BF Field Derived from Doppler UTS Velocimetry", Conf: Computers in Cardiology Sep. 12–, 1978, Stanford, Cal., IEEE CH1391-2/78/0000-0175, pp. 175-178.

"Computer Based Pattern Recognition of Carotid Artery Doppler Signals for Desease Classification: Prospective Validation", Y. E. Langlois, et al., *Ultrasound in Med. & Biol.*, 1984, vol. 10, No. 5, pp. 581-595.

"Analysis and Automatic Classification of Breath Sounds", A. Cohen, et al., *IEEE Transactions on Biomedical Engineering*, Sep., 1984, vol. BME-31, No. 9, pp. 585-590.

"Flow Velocity Patterns in the Carotid Bifurcations of Young, Presumed Normal Subjects", D. J. Phillips, et al., *Ultrasound in Med. & Biol.*, 1983, vol. 9, No. 1, pp. 39-49.

*Primary Examiner*—Francis J. Jaworski
*Attorney, Agent, or Firm*—John C. Moran

[57] ABSTRACT

A system for non-invasively determining the amount of blood flow by performing an autoregressive analysis of Doppler shifted acoustical signals resulting from reflected ultrasonic signals from blood cell movement within internal blood vessels. Each cardiac cycle is determined by an analysis of the patient's electrocardiogram signals, and the resulting cardiac cycles are divided into a predefined number of time segments or channels each containing Doppler shifted signals. The autoregressive analysis is then performed over each individual channel to determine reflection coefficients that model the blood flow and a residual energy level that indicates the energy not accounted for by that modeling. The reflection coefficients results result from a linear predictive code analysis, and the term "reflection coefficients" is not used in the customary manner as defined for ultrasonic flow analysis of blood as defining a level of reflected acoustic energy. A power spectrum analysis is then performed utilizing the reflection coefficients and residual energy level for each channel. Then, the power spectra of individual channels of all of the cycles are averaged together producing a group of averaged channels representing the average blood flow through the patient's internal vessel over all of the cardiac cycles. These averaged power spectra for each combined channel are then normalized and displayed on a channel-by-channel basis utilizing different colors to represent the different power levels. The utilization of different colors greatly enhances the ability of medical personnel to make diagnostic decisions regarding the amount of blood flow.

23 Claims, 10 Drawing Sheets

Microfiche Appendix Included
(5 Microfiche, 45 Pages)

fberg SUBROUTINE cadspect.c PROGRAM cspect SUBROUTINE

NON-INVASIVE BLOOD FLOW MEASUREMENTS UTILIZING CARDIAC CYCLE SYNCHRONIZATION

MICROFICHE APPENDICES

Included in this application are Microfiche Appendices A, B, C, D and E. The total number of microfiche is 5 sheets and the total number of frames is 45.

CROSS-REFERENCE TO RELATED APPLICATIONS

The following applications were filed concurrently with this application and assigned to Bell Telephone Laboratories, Inc., which is assignee-in-part in the present application.

W. T. Hartwell, et al., case 6-2, "Non-Invasive Blood Flow Measurements Utilizing Autoregressive Analysis With Averaged Reflection Coefficients", Ser. No. 738,487; and D. P. Prezas, et al., case 3-3, "Heart Rate Detection Utilizing Autoregressive Analysis", now U.S. Pat. No. 4,616,659.

TECHNICAL FIELD

This invention pertains to the measurement of blood flow by the analysis of Doppler shifted ultrasonic signals. In particular, the invention relates to analyzing the ultrasonic signals utilizing autoregressive techniques and further by utilizing electrocardiogram (EKG) signals to provide a synchronization signal so as to allow the averaging of the results of the autoregressive analysis over a number of cardiac cycles.

BACKGROUND OF THE INVENTION

There exists a well-recognized need for reliable, accurate, and inexpensive blood flow measurement techniques that allow the detection of blood flow abnormalities in both adults and children. This need exists because of the large number of deaths and physical disabilities arising from diseases of the heart and major blood vessels. For example, in 1982, the losses due to early death amounted to 2,100,000 years of potential life that were lost due to heart and peripheral vascular and cerebrovascular diseases before the age of 65 years old. This amounted to almost 46 percent of the deaths in the United States in 1982 being due to diseases affecting blood flow to the brain or the heart. With respect to infants, 28,300 infants died before reaching 28 days of age in 1982, many having intraventricular hemorrhage or perinatal asphyxia (lack of oxygen to the brain around the time of birth). In addition to deaths, a large portion of the surviving infants suffered mental retardation and neurological handicaps due to these two disease categories. These two types of diseases are caused by perturbations in blood flow.

There are two general types of methods for measuring blood flow in humans—invasive and non-invasive techniques. The invasive techniques, are in general: radioactive isotope injection, radioactive organ scanning, positron emission tomography, and angiography. Since these invasive methods involve the use of radioactivity and injection, in general, only one study is performed. The ability to measure blood flow non-invasively and repeatedly in humans would allow the screening of susceptible patients and interruption in the final outcomes of the previously mentioned disease processes. There are two types of non-invasive blood flow measurements: Doppler flow meter and plethysmography. The plethysmography method can only be used in term infants and involves compression of the neck veins and is therefore, rarely used since it can cause an increase of blood in the brain. In addition, this method is not practical for the screening of premature infants.

The Dopoler method is, therefore, the only non-invasive method of performing blood flow analysis and is the only one which can be repeated as necessary. In general, this method involves the transmission of an ultrasound signal through the skin to a blood vessel and the detection of the Doppler shift in the reflected ultrasound signal resulting from the movement of the red blood cells. The Doppler shifted ultrasound signal is then utilized to determine the velocity of the blood flow. This method for measuring the flow of blood is complicated by the fact that in a blood vessel, there are many sets of blood cells moving at different velocities. Each of these sets of blood cells gives rise to a frequency shift, and the resulting Doppler shifted output signal from the flow meter is the sum of the signals from all of the individual sets of cells. This resulting signal is a complex wave comprising a number of different waveforms.

In addition, the analysis of the Doppler shifted signal is complicated by the presence of noise. An example of noise that is present in the Doppler shifted signal is that due to the movement of the blood vessel wall. The wall of a blood vessel moves out during the systole and returns during the diastole portion of the cardiac cycle. It is known in the art to utilize low-frequency filters to reduce the amplitude of the wall movement signals resulting from the diastolic wall movements, but the higher-frequency systolic movements that result in high frequencies are not removed by the low-frequency filters. The latter frequencies cannot be removed since they fall well within the frequency range of the signals resulting from the movement of the red blood cells.

Another problem that arises in attempting to analyze and display the Doppler shifted signal is that the heart rate varies not only from person to person but within a given person over a relatively short period of time. This makes interpretation of the resulting data very difficult since the difference in the cardiac cycle must be included if a diagnosis is to be performed since the resulting display can have a different appearance. This variation from cardiac cycle to cardiac cycle also makes it difficult to perform an averaging over a number of cycles using prior art techniques.

Because of the complexity of the Doppler shifted signal, it is necessary to perform analog or digital analysis of these signals in order to present the information in a manner which is useful to medical personnel attempting to diagnose blood flow rate. At present, there are three major techniques that are utilized to analyze these signals: zero crossing method, phase lock loop (PLL) method, and spectral analysis utilizing Fourier analysis. The most common of these techniques is the zero crossing method. This method involves the utilization of a zero crossing detector on the output of a Doppler ultrasonic flow meter. The zero crossing method is described in detail in the paper by M. J. Lunt, "Accuracy and Limitations of the Ultrasonic Doppler Blood Velocity Meter and Zero Crossing Detector," Ultrasound in Medicine and Biology, Vol. 2, pp. 1–10, Pergamon Press, 1975, GB. The problems with the zero crossing method are that it approximates the mean velocity envelope only in steady-state laminar flow, thus potentially producing significant error in estimating pulsatile flow that exists in human blood vessels. In addition, the method is amplitude dependent, and high-frequency, low-amplitude signals such as blood vessel noise can cause significant waveform distortion. In addition, the resulting waveform from the zero crossing method is difficult to interpret because the output signal is neither proportional to the instantaneous mean nor to the instantaneous peak velocity of the blood flow.

The second method that has been utilized to analyze the Doppler shifted signal is the phase locked loop (PLL) technique. The basic idea behind the PLL technique is to lock a voltage controlled oscillator onto an input signal that is under measurement. A phase detector is used to indicate the relative phase (frequency) difference between the input signal and the output of the voltage controlled oscillator. This difference signal is low-pass filtered and applied back to the voltage controlled oscillator in order to control it. When used to analyze the Doppler shifted signal, the difference signal from the phase detector consists of positive and negative displacements about a center line corresponding to the zero Doppler shift. This techniques is described in greater detail in the article by A. Sainz, V. C. Roberts, and G. Pinardi, "Phase-Locked Loop Techniques Applied to Ultrasonic Doppler Signal Processing," *Ultrasonics*, Volume 14, pp. 128-132, 1976.

The problem with applying the PLL technique to a complex spectra such as the Doppler shifted signal is that this signal is composed of a multitude of frequencies. As a result of this, the PLL apparatus appears to jump from one frequency or another. Since, during operation, the PLL apparatus transiently locks onto the maximum frequency present in the signal giving an indication of the peaks of the envelope of peak frequencies in the Doppler shifted signal. If the difference voltage from the phase detector is averaged for some length of time by an integrator, the resulting signal gives an indication of the mean velocity. Whereas, the PLL technique does give some information concerning the blood flow, it does have definite limitations because of the complex nature of the Doppler shifted signal spectrum and the fact that the cardiac cycle is constantly varying.

The third method of analyzing the Doppler shifted signal is to do a Fourier transform spectrum analysis of the Doppler shift signal. The resulting output from the Fourier analysis is a signal which plots the power level of each particular frequency present in the signal against time. This method gives an indication of the instantaneous velocity patterns which occur during each individual cardiac cycle. This technique is described in *Non-Invasive Clinical Measurements*, J. P. Woodcock, London, Pittman Medical, 1977, Chapter 6, pp. 82-88, and utilization of this method is described in the papers by Y. Langlois, J. O. Roderer, A. Chang, D. J. Phillips, K. W. Beach, D. Martin, T. M. Chikos, and D. E. Strandness, Jr., "Evaluating Carotid Artery Disease—The Concordance Between Post Doppler/Spectrum Analysis and Angiography," Ultrasound in Medicine and Biology, Vol. 9, No. 1, pp. 51-63, 1983; and R. W. Barnes, S. E. Rittgers, W. W. Putney, "Real Time Doppler Spectrum Analysis—Predictive Value in Defining Operable Carotid Artery Disease," Archives of Surgery, Vol. 117, pp. 52-57, January, 1982.

Whereas, the Fourier analysis of the Doppler shift signal gives an indication of the energy at each of the Fourier harmonics of the waveform, the technique does suffer from certain problems. The primary problem of using the latter analysis of the Doppler shifted signal is that the Fourier analysis is based on the premise that the frequency components can have any relationship to each other including an extremely close relationship between the different frequencies. Because of this basic assumption, the Fourier analysis attempts to find harmonics to describe a complex signal in which the frequency components are close in phase and frequency. The problem with this assumption with respect to Doppler shifted signals resulting from blood flow is that the latter comprise only a few frequency components that are reasonably well spaced from each other in frequency.

Since the assumption of the Fourier analysis is that the signal is far more complex than it actually is, the resulting display from a Fourier analysis of the Doppler shifted signal tends to be extremely complicated, thus making visual representation difficult. This complex visual representation is further complicated by the fact that the cardiac cycle is varying making diagnosis difficult because the display is changing in a very complex manner.

Another problem that exists with utilizing Fourier analysis is that this type of analysis is very sensitive to the starting point of the signal under analysis. This factor comes into effect when an attempt is made to average the results from a number of Fourier analyses of individual cardiac cycles. Averaging is desirable to obtain accurate information. Techniques such as those described in the previously mentioned article by Langlois, et al., in which an EKG signal is used to indicate a relative starting point for the cycle still suffer from this problem since the precise starting point must be repetitively determined for the Fourier analysis technique. This is also complicated by the fact that the length of the cardiac cycles and the amount of blood flowing in these cycles varies with time. This further complicates the Fourier analysis by making it difficult to average the results of the cycle and also because when the results of the Fourier analysis are displayed, the resulting display appears quite different for different lengths of the cardiac cycle.

Another problem with the utilization of Fourier transform spectrum analysis of the Doppler shift signal is the relative cost of the equipment to do Fourier analysis. The additional cost of the instrumentation when the Fourier analysis circuitry is added, approximately increases the basic cost by four times. The additional cost for Fourier analysis is due to the fact that this analysis requires extremely intense mathematical calculations.

From the previous paragraphs it can be seen that there exists a need for an analysis technique which more closely models the fundamental nature of the Doppler shift signals and which also can be provided at a greatly reduced cost than the existing analysis techniques. In addition, there exists a need for a method of analysis that both accurately portrays the spectrum and allows the results of the spectrum analysis to be averaged over a number of cycles without introducing erroneous data in the results. In addition, there is a need for an analysis technique that presents to medical personnel a display which in a simple visual representation provides them with fundamental information on whether the blood flow is normal or abnormal.

SUMMARY OF THE INVENTION

In an illustrative method and structural embodiment, a departure in the art is achieved by performing an autoregressive analysis of reflected Doppler shifted ultrasonic signals resulting from blood cell movement to determine the amount of blood flow. The autoregressive analysis closely models the blood flow within a patient's internal blood vessel and can be performed on economical computers since it is not calculation intense. Each cardiac cycle of a patient is divided into a predefined number of time segments or channels by first determining the start and end of each cardiac cycle from electrocardiogram signals obtained from the patient. The autoregressive analysis is then performed on each individual channel calculating the power spectrum for that channel. Then, in order to present an easily interpreted display for medical personnel, the power spectra for corresponding channels for a plurality of cardiac cycles are averaged and normalized together, and the averaged and normalized power spectra for the channels are displayed using different colors to represent different power levels thus greatly enhancing the ease of interpretation.

Advantageously, a blood flow analysis system for measuring the amount of blood flow within internal patient vessels comprises a Doppler flow meter for transmitting a beam of ultrasonic frequency acoustic signals into the patient vessel and for receiving the reflected acoustical signals from blood cells moving within the vessel. In response to the reflected signals, the flow meter then determines the amount of Doppler shift between the transmitted and the received signals. An analog-to-digital converter is subsequently used to convert the analog Doppler shifted signals into digitized samples of Doppler shifted signals. An electrocardiogram instrument monitors the patient's electrocardiogram signals, and these signals are digitized by a second analog-to-digital converter. A first set of program instructions that is executed by computer are responsive to the digitized electrocardiogram signals to determine the start and end of each cardiac cycle. A second set of instructions is responsive to the start and end of the patient's cardiac cycle and the digitized Doppler shifted signals to divide the latter signals into a predefined number of time segments each representing the same amount of time with the total amount of time for all time segments equal to one cardiac cycle. A third set of program instructions is responsive to the digitized Doppler shifted signals for each time segment to determine the power spectrum of the digitized Doppler shifted signals for that particular time segment thereby determining the amount of blood flow within the patient's internal vessel.

Advantageously, the power spectrum for each time segment for a plurality of cardiac cycles is calculated and stored by a fourth set of program instructions. A fifth set of program instructions calculates the total energy of the digitized Doppler shifted signals for each particular time segment for a plurality of cardiac cycles, and a sixth program divides the stored power spectrum by each of the calculated total energy amounts for each time segment to produce a normalized power spectrum for each time segment. Finally, a seventh program averages all the normalized power spectra for individual time segments for the plurality of cardiac cycles.

Also, the average spectrum for each time segment is displayed by an eighth set of program instructions utilizing different colors to represent different power levels thus enhancing the interpretability of the displayed power spectra.

Advantageously, the third set of program instructions performs an autoregressive spectrum analysis. In addition, these latter program instructions comprise a number of subsets of program instructions. The first subset of program instructions is responsive to the digitized Doppler shifted signals of each of said time segments for calculating reflection coefficients modeling the blood flow. The term "reflection coefficients" are entities calculated using linear predictive code (LPC) analysis techniques and are not equivalent to terms referring to a level of reflected acoustic energy as is common in blood flow analysis using ultrasonic methods. A second subset of program instructions is responsive to the Doppler shifted sampled signals and the calculated reflection coefficients for generating a residual energy level for each of the time segments representing the energy not accounted for by the modeling performed by the reflection coefficients. A third subset of program instructions is responsive to the residual energy level and the reflection coefficients for each of the time segments for calculating the power spectrum of the digitized Doppler shifted signals within that time segment.

A method for determining the amount of blood flow by utilization of a system comprising a Doppler flow meter, electrocardiogram instrument, analog-to-digital converters, and a digital computer, performs the following steps: determining the start and end of a patient's cardiac cycle by analysis of digitized signals from the electrocardiogram instrument, digitizing the Doppler shifted signals from the flow meter by utilization of an analog-to-digital converter, dividing the resulting digitized Doppler shifted signals into a predefined number of time channels, and spectrum analyzing the Doppler shifted signals for each channel to determine the power spectrum for that channel. The power spectrum is indicative of the amount of blood flow flowing within internal blood vessels of the patient.

Advantageously, the method further comprises the steps of storing the resulting power spectrum of the Dopoler shifted signals for a plurality of cardiac cycles, calculating the total energy of all the Doppler shifted signals of each particular time channel over the plurality of cardiac cycles, dividing the resulting power spectrum by the total energy to obtain a normalized power spectrum which eliminates the variations caused within the Doppler flow meter from cycle to cycle, and averaging all the normalized power spectra of the individual time channels for the plurality of cardiac cycles.

Also, the ease with which medical personnel can analyze the amount of blood flow is enhanced by displaying the average power spectrum for each time channel utilizing different colors to represent the different power levels. This manner of displaying greatly enhances the ease of interpreting the resulting display.

Advantageously, the spectrum analyzing step is performed by the steps of calculating reflection coefficients that model the blood flow within the patient's vessel for each time channel, generating a residual energy level for each time channel to account for the energy within the signals from the flow meter that are not accounted for by the modeling performed by the reflection coefficients, and computing the power spectrum for each time channel from the residual energy level and the reflection coefficients for each time channel.

DETAILED DESCRIPTION

Figure 1:
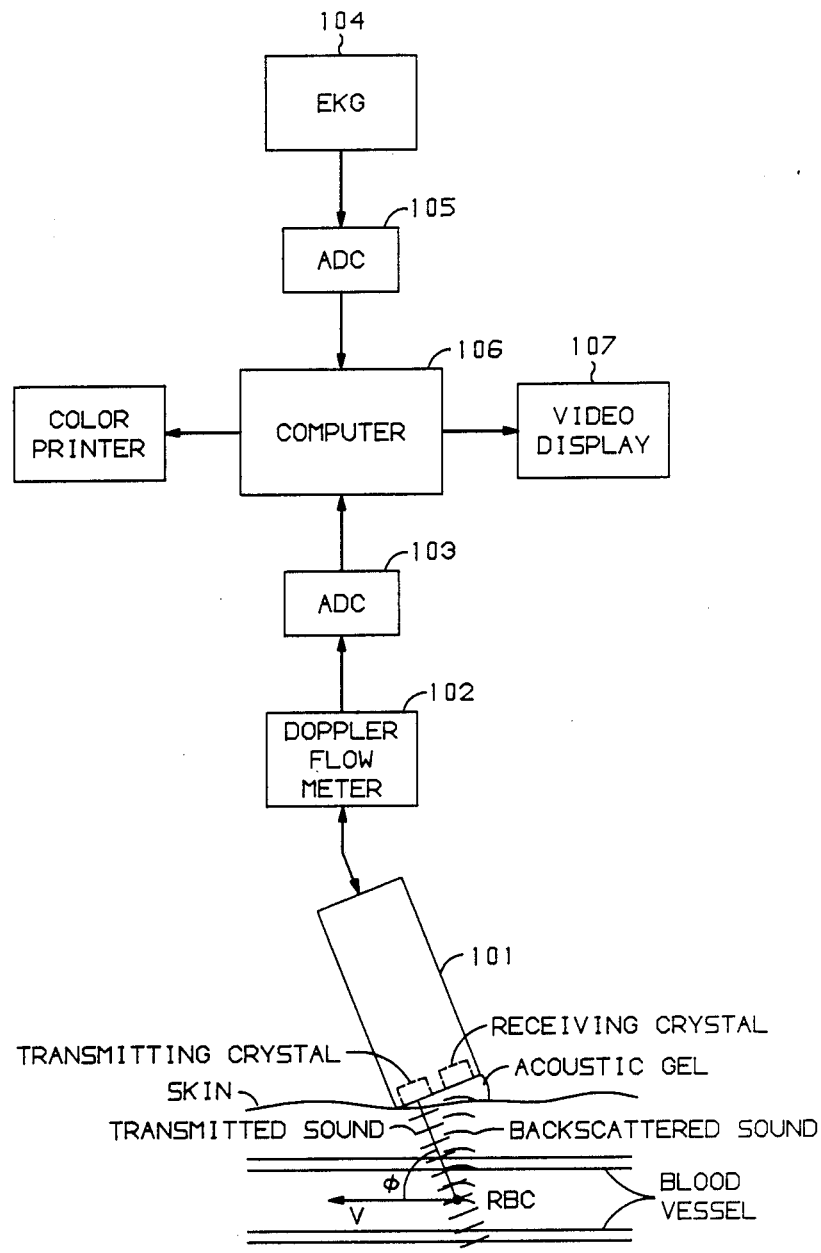
FIG. 1 illustrates, in block diagram form, a blood flow analysis system in accordance with this invention.

A system for analyzing and displaying the flow of blood within a blood vessel is illustrated in FIG. 1. Doppler flow meter 102 and ultrasonic transducer 101 generate an analog Doppler shifted signal that corresponds to the speed of the red blood cells (RBC) that are moving in a blood vessel. The frequency of the signal indicates the speed at which the blood cells are moving, and the power observed at a particular frequency indicates the number of blood cells moving at that frequency. Because of such factors as the angle of the probe and other complex physical factors, the energy does not literally correspond to the number of red cells. However, the energy is roughly proportional to the number of cells moving at any given speed.

The Doppler shifted signal is converted to digital form by analog-to-digital converter 103. Initially, computer 106 is responsive to the digitized Doppler shifted signal to store the signals along with the EKG signal from electrocardiogram unit 104 digitized in converter 105. After the information for a number of cardiac cycles has been stored, computer 106 is responsive to the digitized Doppler shifted signals and digitized EKG signals to calculate the spectral power present at the various frequencies, to average the spectral powers for a number of cycles together, and to display this average over the time required for one cycle.

Figure 2:
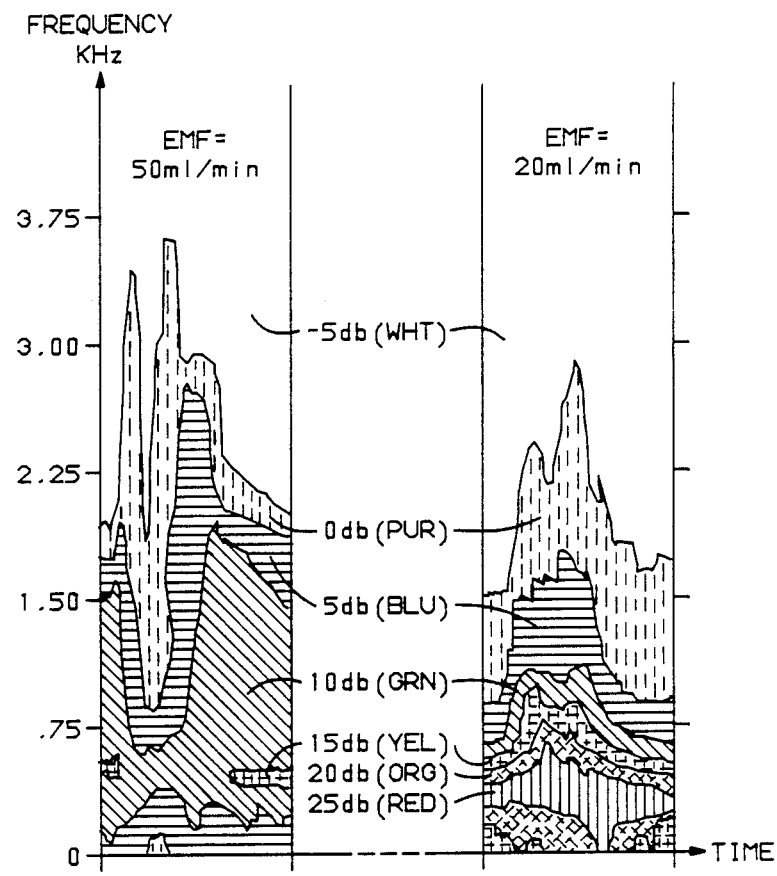
FIG. 2 illustrates, in graphic form, the results of analysis performed by the blood flow system illustrated in FIG. 1 on the flow of blood within an artery of a piglet.

FIG. 2 illustrates the information that is displayed by computer 106 in analyzing the blood flow. Illustrated in FIG. 2 are the results of tests performed on a piglet weighing approximately 4.2 kilograms and whose blood flow was artificially controlled. In addition, the blood flow was monitored using electromagnetic flow meter which does require surgical procedures. The results of the electromagnetic flow meter (EMF) is shown in the upper portion of FIG. 2. FIG. 2 comprises the results of two different tests that were performed by controlling the blood flow at different rates. The difference between a flow rate of 50 milliliters per minute and a flow rate of 20 milliliters per minute (as determined by an EM flow meter) is quite apparent in FIG. 2 and readily discernible by medical personnel. Each test is divided into a number of time segments referred to as channels; and illustratively, there may be 50 channels per cardiac cycle. The averaging of power is done on a per-channel basis. For example, the power for channel 1 in each cycle are averaged together. The display illustrated in FIG. 2 is produced by accurately determining the start of each cardiac cycle and end of this cycle by analyzing the EKG signals. Once the start and end of the cardiac cycle is determined, then the digitized Doppler shifted signals in this time period are illustratively divided up into the 50 channels. An autoregressive analysis is performed on all of the points in a given channel to determine the power spectrum of that channel. Illustratively, some implementations of autoregressive analysis are, for example, the Maximum Entropy technique or Autocorrelation Coefficients technique using Durbin-Levinson Recursion. After the power spectrum of all channels has been calculated, the operator is given the opportunity to include or not include this calculated power in the total power of the previous cycles that have been calculated. If the operator chooses to include the powers of this cycle into the total, then the spectrum power of each channel of the present cycle is included with the totals of the previous cycles. After all the channels for all the cardiac cycles have been performed, the averages of the channels for the selected cycles are displayed with different colors being used to indicate different power levels.

Figure 3:
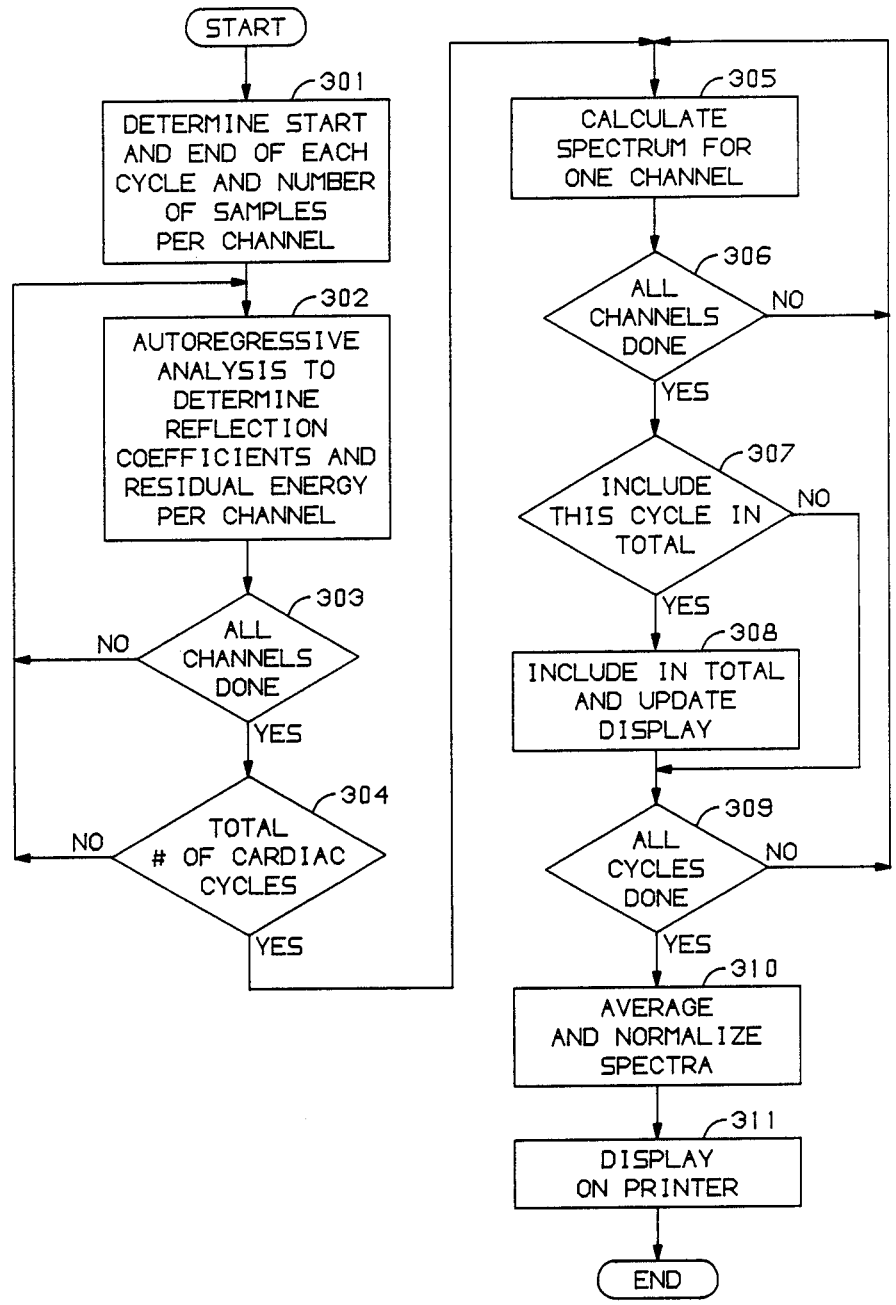
FIG. 3 illustrates, in flowchart form, the programs executed by computer 106 of FIG. 1 in performing the blood flow analysis.

FIG. 3 illustrates in greater detail the steps necessary to produce a display such as illustrated in FIG. 2. For each cardiac cycle, block 301 determines the start and end of the cycle and the number of samples per channel. Reflection coefficients and residual energy for each channel are then determined by blocks 302, 303, and 304. Block 302 performs a autoregressive analysis of the samples for one channel to determine the reflection coefficients and the residual energy. The reflection coefficients define a model constructed by the autoregressive analysis of red blood cell movement. The residual energy is the amount of energy unaccounted for by the model. The reflection coefficients and residual energy are later used by block 305 to determine the spectrum for each channel.

After all of the channels for the cycles have been analyzed, the power spectra of channels for all cycles are calculated and averaged together by blocks 305 through 310. The calculations for a particular spectrum of one channel are performed over a multitude of frequencies and utilize the reflection coefficients and residual energy for this particular channel as calculated in block 302. Averaging also is performed over a multitude of frequencies for each channel. During this process, an operator is allowed to determine which cycles will be included into the final output by selecting the cycles to be included. For each cycle, blocks 305 and 306 determine the spectrum for each channel. Once the spectra for an entire cycle has been calculated, the operator is given the option of including the results of the calculations for the present cycle in a total of past cycles by decision block 307. The latter displays to the operator the spectra calculations for the present cycle and the average of the spectra calculations for past cycles. If the operator decides to include the present cycle, then block 303 includes the results of the present cycle's calculations in the totals maintained for the past cycles.

After each cycle is completed, decision block 309 checks to see whether or not all cycles have been processed. If all cycles have been processed, then block 310 is executed. The latter averages the totals for each channel by individual frequencies for all of the displays and then normalizes these resulting averages in order to take out variations due to differences of gain in the Doppler flow meter 102. The results of block 310 are then displayed on a color printer by block 311. Advantageously, this printer may be the Tektronix Model 4695 Ink Jet Printer.

Autoregressive spectrum analysis of block 302 assumes an analysis model based on LPC techniques given by:

$$E(z) = X(z) F(z) \qquad (1)$$

where:
- E(z) is the z-transform of the input signal,
- X(z) is the z-transform of the output signal, and
- F(z) is an all pole filter.

In the sample domain, equation 1 can be written as follows:

$$e(n) = \sum_{m=0}^{ORDER} fc(m)x(n-m) \qquad (2)$$

which can be rewritten as $$e(n) = x(n) - \sum_{m=1}^{ORDER} fc(m)x(n-m) \qquad (3)$$

where x(n) represents the present time sample, fc represents filter coefficients, and ORDER represents the number of filter elements.

As described in J. D. Markel and A. H. Gray, "Linear Prediction of Speech", Springer-Verlag, Berlin Herdelberg New York, 1980, on page 10, the input signal e(n) can be interpreted as the prediction error between the actual data sample x(n) and the linear combination of the previous n samples given by $$\sum_{m=1}^{M} fc(m)x(n-m).$$

Since the input signal, minus the predicted signal can be interpreted as an error, the common analysis procedure is to minimize the sum of the squares of this error as a method for determining the filter coefficients.

Many autoregressive techniques have been developed to minimize this error term; and the one utilized here is the Berg Maximum Entropy method which is described in the paper by L. Marple, "A New Autoregressive Spectrum Analysis Algorithm", IEEE Trans. on Acoustics, Speech, and Signal Processing, vol. ASSP-28, No. 4, August, 1980, pp. 441–454. The Berg method solves for the filter coefficients, fc(m), by using both a forward and backward prediction errors. For any given point, the error is calculated by considering the points in time preceding the sample point under calculation and points prior to the particular point under consideration. The forward error is defined by:

$$f_{err}(k) = \sum_{i=0}^{ORDER} fc(i) * x(k - ORDER - i) \qquad (4)$$

while the backward error is defined by:

$$b_{err}(k) = \sum_{i=0}^{ORDER} fc(i) * x(k+i) \qquad (5)$$

where the values of index k range from 1 to (NPTS−ORDER) and fc(0) is defined as 1. NPTS is the number of sample points in the channel being analyzed. Using these two expressions, the problem is to determine the set of filter coefficients that minimize the sum of both the forward and backward errors summed over all sample points subject to a constraint. Thus, the error to be minimized is given by the following equation:

$$error = \sum_{k=1}^{NPTS-ORDER} f_{err}(k) * f_{err}(k) + b_{err}(k) * b_{err}(k). \qquad (6)$$

The constraint on the values of fc is that they satisfy the relation $$fc(k) = FC(k) + rc(ORDER) * FC(ORDER - k) \qquad (7)$$

where: fc(ORDER) = rc(ORDER).

where FC represents the coefficients determined when ORDER−1 terms were used in the prediction equation. This relation is called the Levinson recursion, and the term, rc(ORDER), is frequently referred to as the LPC reflection coefficient.

The filter coefficients fc(k) can be solved for in equation 6 by substituting equations 4 and 5 into equation 6 and taking the partial derivative of this equation with respect to fc(ORDER). The resulting equation is a recursive formula given in terms of the reflection coefficient as follows:

$$rc(ORDER) = \frac{-2 \sum_{k=1}^{NPTS-ORDER} b_{err}(k) f_{err}(k+1)}{\sum_{k=1}^{NPTS-ORDER} ||b_{err}(k)|^2 + |f_{err}(k+1)|^2|} \qquad (8)$$

Figure 5:
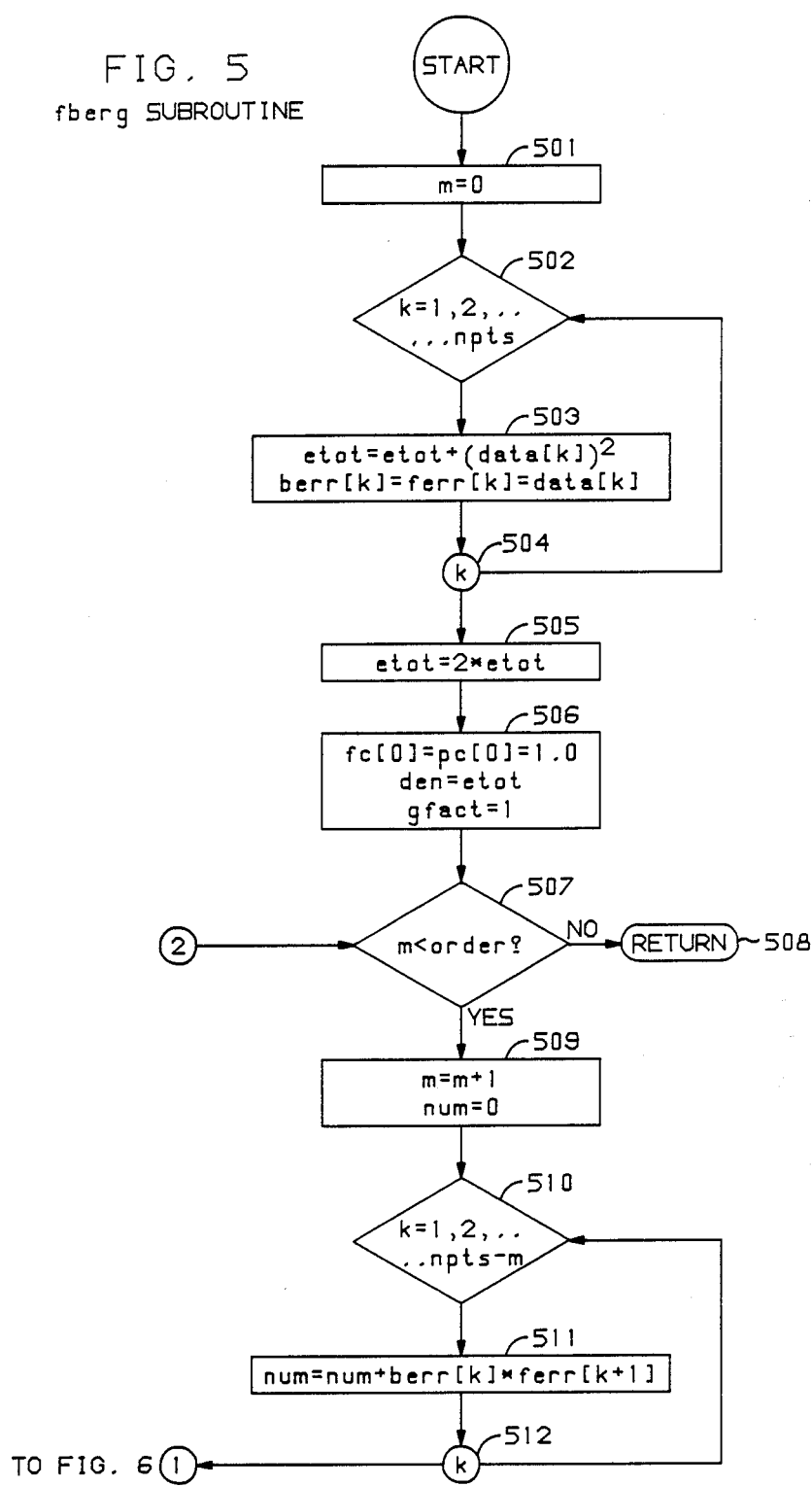
FIGS. 5 and 6 illustrates in greater detail, the program steps of block 409 of FIG. 4.
Figure 6:
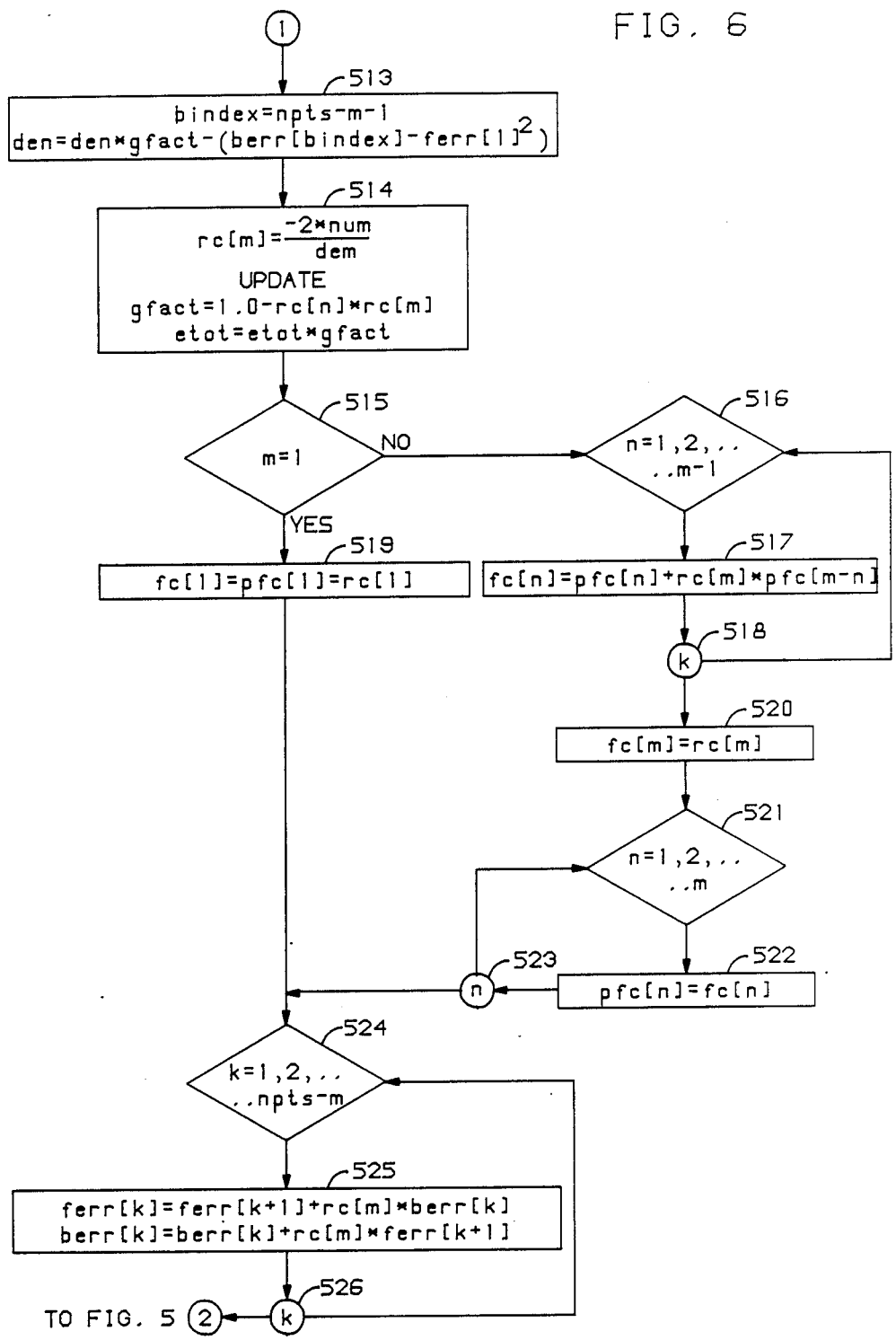

FIGS. 5 through 6 illustrate a program for evaluating equation 8.

Given the filter coefficients, the power spectrum for any frequency, f, is given by $$P(f) = \frac{PE}{ABS\left|1 + \sum_{k=1}^{ORDER} fc(k) * e^{(-2\pi * i * f * /fsample)}\right|^2} \qquad (9)$$

where fsample is the frequency at which the original signal was sampled, P(f) is the power at the particular frequency f, and PE is a measure of the residual energy left over in the autoregressive analysis. ABS represents the magnitude function of a complex number.

The programs illustrated in later material by flowcharts and program listings require equation 9 to be transformed to equation 10 for the following reasons. The power is computed in db to avoid large numbers. Thus, log(P(f)) is the quantity calculated. Also, since the programs are written in the C programming language, which does not have complex arithmetic, the exponential factor is broken down into real and imaginary parts. For these reasons, equation 9 is transformed into the following:

$$10 * \log(P(f)) = 10 * \log(PE) - 20 * \log(ABS) \qquad (10)$$

$$\left|1 + \sum_{k=1}^{ORDER} fc(k) * \{\cos(k * f * arg) + i * \sin(k * f * arg)\}\right|$$

where arg = 2*π/fsample. The equations 4 through 10 give a mathematical description of the process required to implement the flowchart of FIG. 3.

Now consider in greater detail, the various programs that are required to perform the previous equations.

Figure 4:
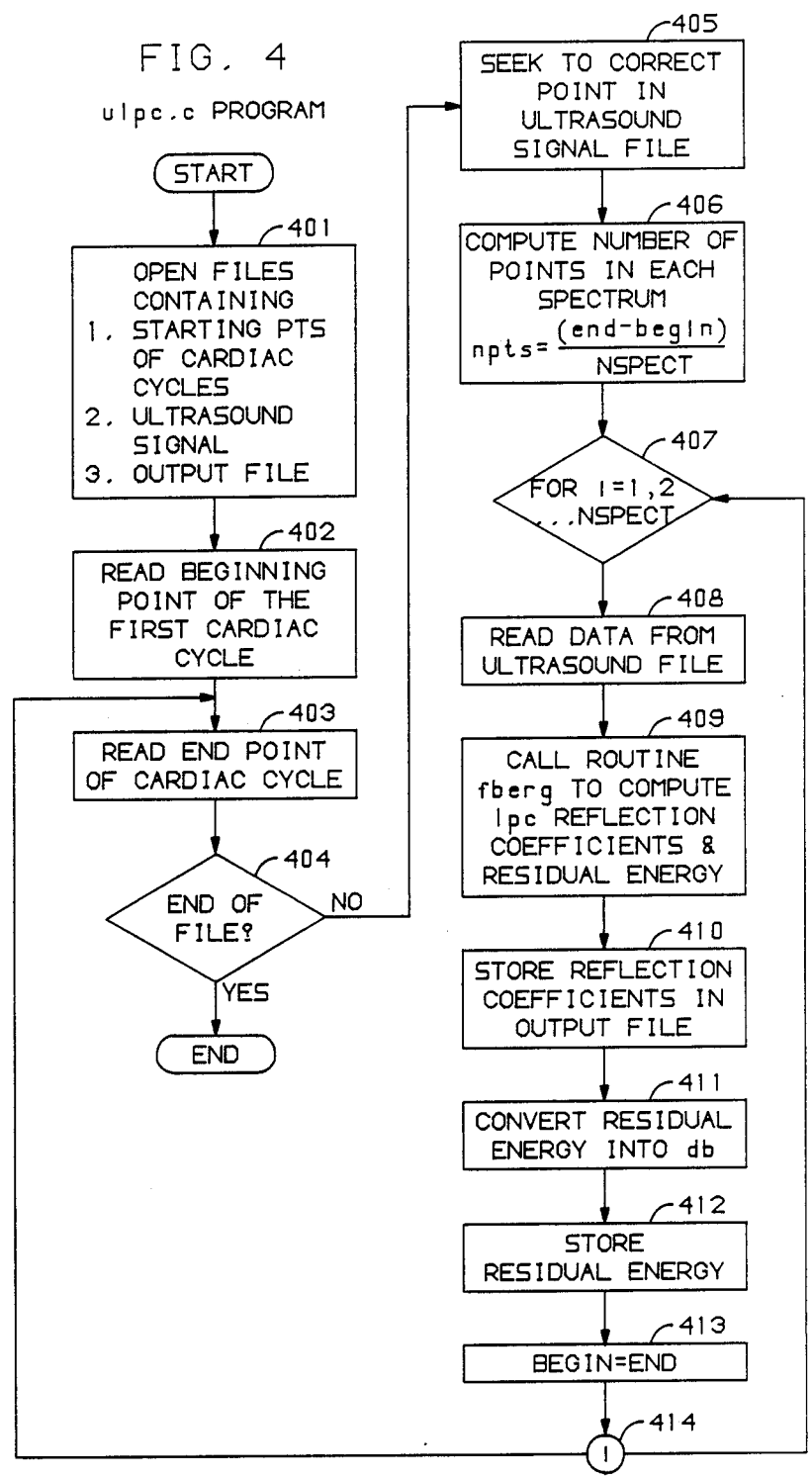
FIG. 4 is a detailed flowchart of the program steps executed by blocks 302 through 304 of FIG. 3.

The process of performing the autoregressive analysis, as defined in block 302 of FIG. 3, is shown in greater detail in the flowchart illustrated in FIG. 4 and in Appendix A as routine ulpc.c. As illustrated in FIG. 4, the program first opens the necessary files, block 401, in order to gain access to the digitized Doppler signal and the points which define the start and end of the cardiac cycles. Block 402 first reads the beginning of the first cycle and blocks 403 and 404 checks if the entire file has been read. If the entire file has been read, then the program is finished. However, if the entire file has not been read, block 405 utilizes the starting point of the cardiac cycle to seek to the proper place in the Doppler signal file. Block 406 then computes the number of sample points for each channel by dividing the total number of samples by the number of channels. Illustratively, the number of channels is 50. Blocks 407 through 414 then compute the reflection coefficients and residual energy for a particular channel. For each channel, the data samples of that channel are utilized to calculate the reflection coefficients and the residual energy in block 409. The latter block implements the Berg method by utilizing subroutine fberg which is illustrated in FIGS. 5 through 6 and a program listing is given in Appendix B. The reflection coefficients are then stored in an output file by block 410. The reason for storing reflection coefficients rather than the filter coefficients themselves is that the reflection coefficients are bounded between 1 and −1 whereas the filter coefficients can be quite large or small. The residual energy is converted to db and stored by blocks 411 and 412. Blocks 413 and 414 determine whether or not all the points of the channel have been utilized. If they have, then the program returns to block 403 to process another cycle.

The fberg subroutine is illustrated in greater detail in FIGS. 5 and 6. This subroutine calculates equation 8 and verifies that the conditions of equation 7 have been met. The fberg routine calculates equation 8 in a recursive manner by first calculating the first reflection filter coefficient for order 1 and then uses this information to calculate a new set of filter coefficients for order 2. Because of this recursive nature, fberg routine is repetitively recalculating equation 8. Blocks 501 through 506, illustrated on FIG. 5, perform the initialization of the various variables used by the subroutine. The initial residual energy, etot, is set equal to the sum of the squares of all the data points of the channel and the backward and forward errors (berr and ferr, respectively) are set equal to corresponding data samples, where the data sample is the digitized Doppler signal. The filter coefficients are initially set equal to 1 by block 506 and the denominator of equation 8 is set equal to the initial residual energy as determined by block 503.

FIGS. 5 and 6 illustrate the evaluation of equation 8. Block 507 determines whether or not the equation has been sufficiently evaluated for the order filter being calculated, and if it has, a return is executed to the program illustrated on FIG. 4 via return block 508. If the filter has not yet been calculated to a sufficient order, then block 509 is executed. The numerator and denominator (num and den, respectively) of equation 8 for this particular order are evaluated by blocks 510 through 513. After the numerator and denominator have been determined, then the reflection coefficient, rc[m], and residual energy for this particular order are evaluated in block 514. Once the reflection coefficient for this order has been determined, then the stepup function is implemented by blocks 515 through 519 to update the previously determined filter coefficients for (ORDER − 1) as defined by the Levinson recursion formula and given in equation 7. The highest order filter coefficient is always equal to the reflection coefficient and is set equal to the reflection coefficient by block 520. The past filter coefficients are then updated by blocks 521 through 523 in order for block 517 to evaluate the next set of filter coefficients. The past filter coefficients are designated as FC(n) in equation 7, and as pfc[n] on FIGS. 5 and 6. The forward and backward errors are next updated by blocks 524 through 526 in order to evaluate blocks 511 and 513 in the next iteration. After the forward and backward errors have been updated, control is passed from block 526 to decision block 507 which determines whether or not all the orders have been evaluated.

Referring back to FIG. 3, once the autoregressive analysis has been performed in blocks 302 through 304, the power spectrum for each channel must be calculated for a plurality of frequencies as defined in equation 10. Illustratively, for each channel, equation 10 is evaluated for 150 different frequencies by blocks 305 and 306. The operator is given the opportunity to include the power spectra just calculated for the present cycle into the total power spectra calculated for previous cycles by blocks 307 through 309. After all of the power spectra has been calculated for the cycles, the resulting power spectra are averaged and normalized by block 310 and then printed by block 311.

Figure 7:
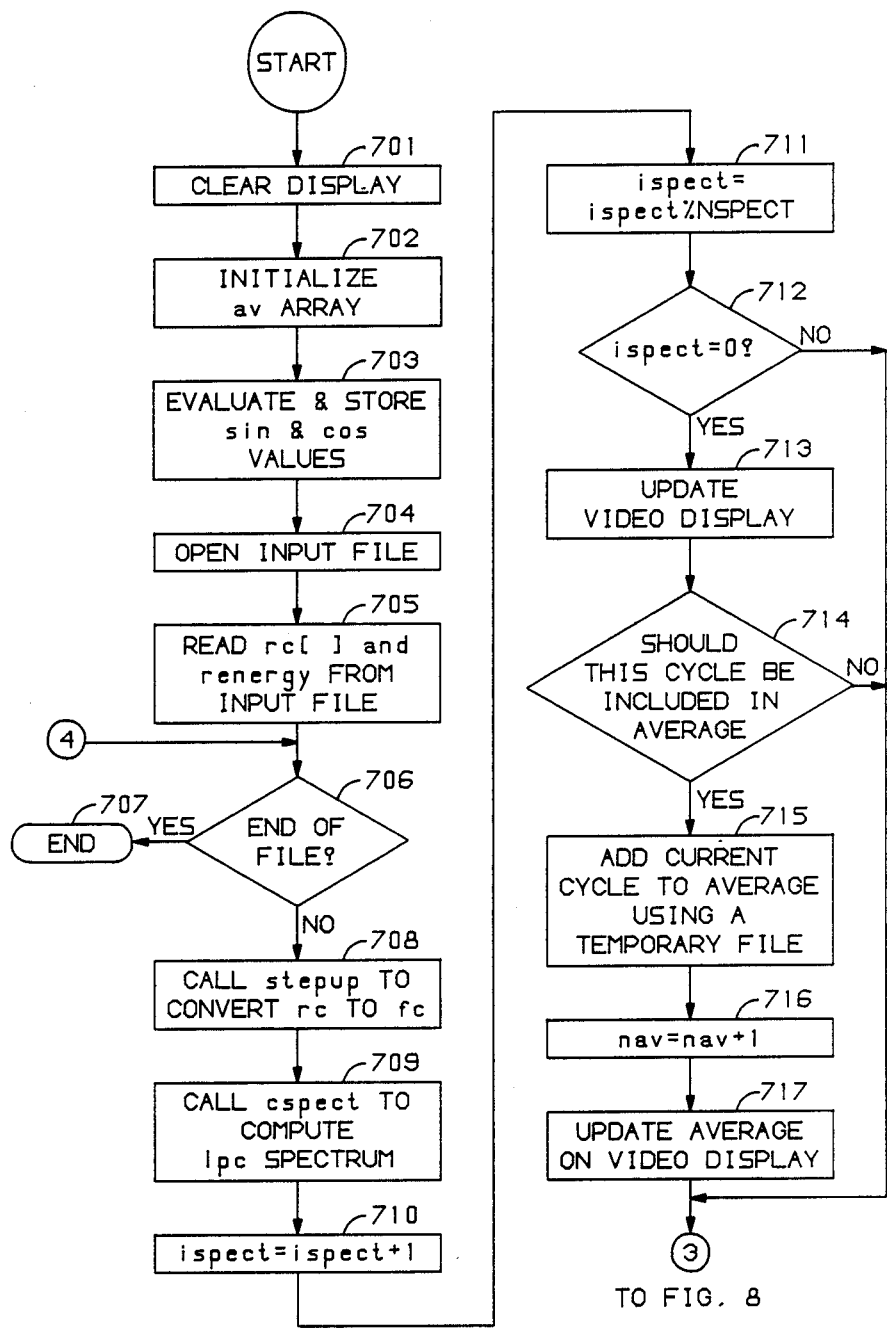
FIGS. 7 and 8 are detailed flowcharts of blocks 305 through 310 of FIG. 3.
Figure 8:
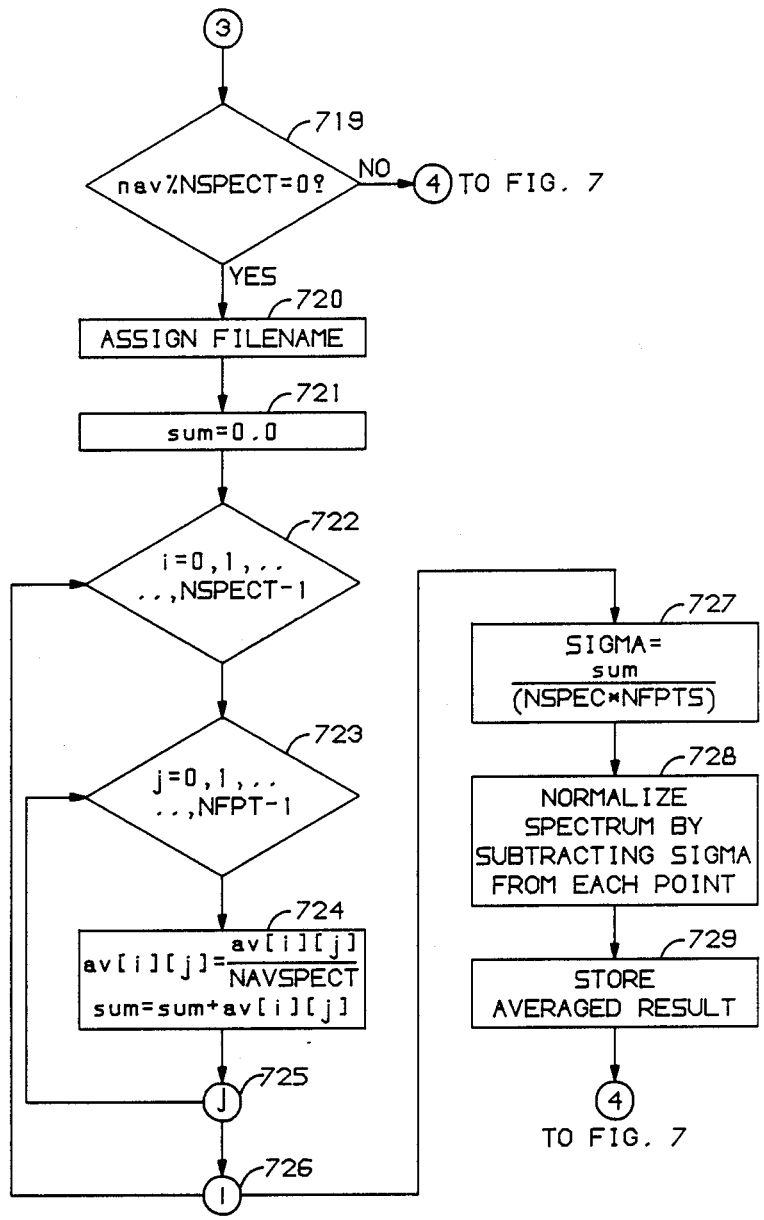

Blocks 303 through 310 are implemented by the cadspect.c program which is illustrated as a flowchart in FIGS. 7 and 8 and as a program listing in Appendix C. Blocks 701 through 704 perform the initialization required for the execution of the cadspect.c program. The sine and cosine values of equation 10 are initially evaluated and stored so as to save processing time. The av array which is used to hold the averages for the spectra for the different channels is initialized to a 0. For each channel, the spectrum is computed by blocks 705 through 712. After the spectra for all channels of a cycle have been calculated, then the operator is given the opportunity to include the spectra results of the present cycle with past cycles by blocks 713 through 717. Once the maximum number of cycles have been processed, then blocks 720 through 729 are executed to perform the normalizing and averaging of the spectra across cycles for particular channels as depicted in block 310 of FIG. 3.

Figure 9:
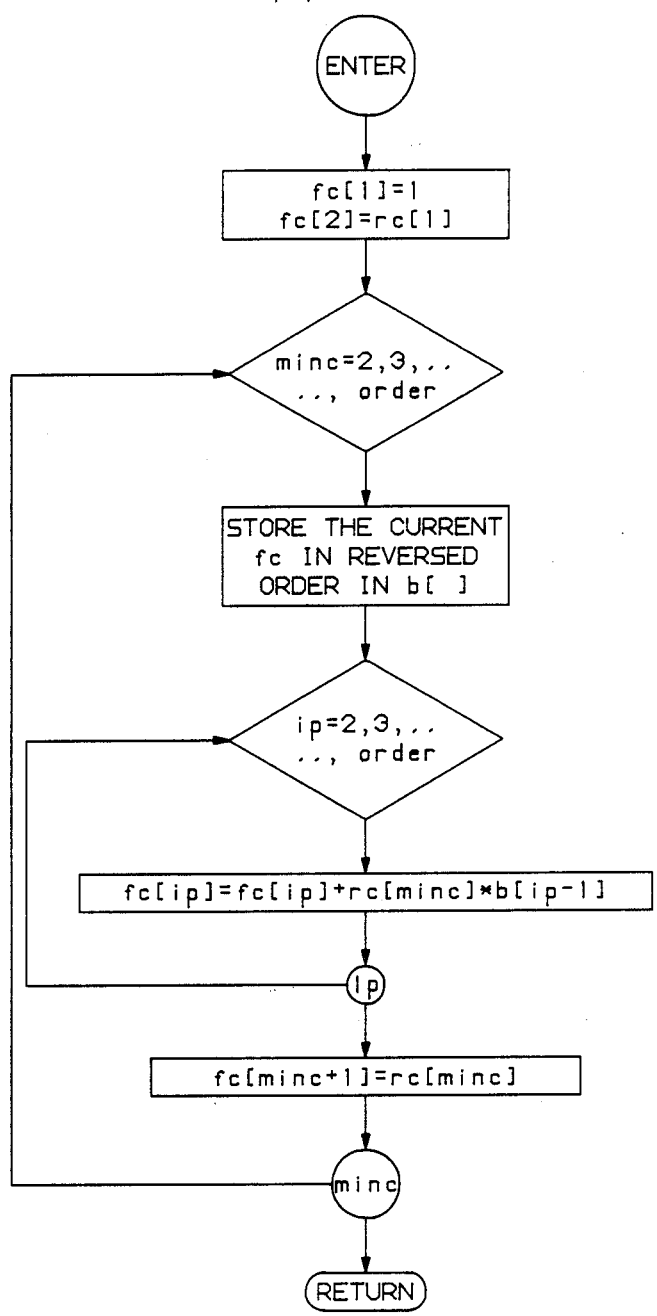
FIG. 9 is a detailed flowchart of block 708 of FIG. 7.
Figure 10:
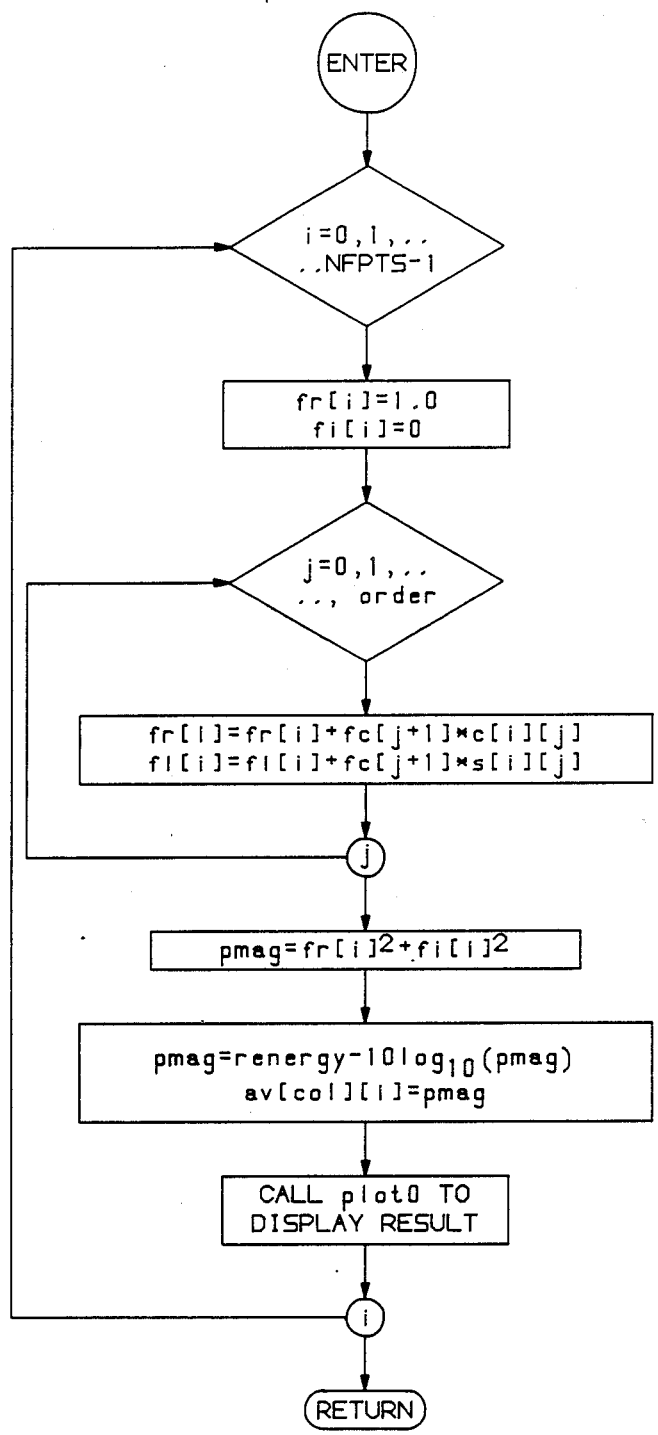
FIG. 10 is a detailed flowchart of block 709 of FIG. 7.

Consider now in greater detail, FIGS. 7 and 8. The calculation of the spectrum for each channel is performed by blocks 705 through 711. After reading the reflection coefficients, rc[], and the residual energy, which is referred to as renergy, the program checks to see if it is at the end of a file; if not, it executes block 708 which converts the reflection coefficients into the filter coefficients by executing the stepup subroutine that implements equation 7. This subroutine is illustrated in FIG. 9. Once the spectrum for this particular channel has been computed, block 710 advances the spectrum counter and blocks 711 and 712 determine whether or not all the channels for this particular cycle have been computed. If not all of the channels have been computed, then block 705 is once again calculated.

If the spectra for all of the channels has been calculated, then the video display is updated with the newly computed spectra for the present cycle by block 713, and the operator is given the opportunity to either include or not to include this cycle in the total of past cycles by block 714. At this time, the spectra average of past cycles is being displayed as well as the spectra for the present cycle. If the operator chooses to include the present cycle with the average of past cycles, then blocks 715 through 717 are executed. The latter blocks included the current cycle into the total of the previous cycles.

Next, decision block 719 determines whether or not the computations have been performed for all cycles. If the computations have not been performed for all cycles, then block 705 is once again executed. If the computations have been performed for all of the cycles, then blocks 720 through 729 are executed implementing blocks 310 and 311 of FIG. 3 which average, normalize, and display the resulting spectra of all of the cycles. In addition, the normalized spectrum is stored in a file from which at some later point in time this can be reproduced on a color printer such as Tektronix Corporation, Model 4695. A program for performing the display of a normalized spectrum on such a color printer is the tekcopy program which is listed in Appendix D.

A program for performing the determination of the start and end of each cycle as shown in block 301 of FIG. 3 is illustrated in program form in Appendix E. Further explanation of this program is given in the copending application of Prezas, et al.

It is to be understood that the above-described embodiment is merely illustrative of the principles of this invention; other arrangements may be devised by those skilled in the art without departing from the spirit and the scope of the invention.

What is claimed is:

1. A blood flow analysis system for measuring velocity of blood moving within internal patient structures, comprising:
   means for transmitting ultrasonic frequency acoustic signals into said patient structures;
   means for receiving reflected acoustical echo signals from blood flows within said structures;
   means for determining signals representing the difference between said transmitted and said received signals;
   means for sampling the difference signals;
   means for determining the start and end of said patient's cardiac cycle in response to the patient's electrocardiogram signals;
   means responsive to the determined start and end of said patient's cardiac cycle and said sampled difference signals for dividing said sampled difference signals into a predefined plurality of time segments of signals each representing the same amount of time of said segment plurality with the total amount of time equal to one cardiac cycle;
   means for autoregressive spectrum analyzing each of said time segments of said sampled difference signals to determine the power spectrum of said sampled difference signals for each of said time segments; and
   means responsive to the determined power spectrum of each of said time segments for determining the blood velocity within said internal patient structures indicating blood flow.

2. The system of claim 1 further comprising means for storing said determined power spectrum of said sampled difference signals of each of said time segments for a plurality of cardiac cycles;
   means for calculating the total energy of all of the sampled difference signals of each particular time segment for said plurality of cardiac cycles;
   means for dividing the stored power spectrum by said total energy for each of said segments to produce a normalized power spectrum; and
   means for averaging all normalized power spectra of individual time segments for said plurality of cardiac cycles.

3. The system of claim 2 further comprising means for displaying said average power spectrum for each time segment with different colors representing different power levels.

4. The system of claim 3 wherein said spectrum analyzing means comprises:
   means responsive to said sampled difference signals of each of said time segments for calculating reflection coefficients modeling said blood flow;
   means responsive to said sampled difference signals and said reflection coefficients for generating a residual energy level for each of said time segments representing the energy not accounted for by said modeling; and
   means responsive to said residual energy level and said reflection coefficients for each of said time segments for calculating the power spectrum of said sampled difference signals for each of said time segments.

5. An ultrasonic Doppler system for measuring velocity of objects moving within internal patient structures, comprising:
   means for transmitting ultrasonic frequency acoustic signals into said patient structures;
   means for receiving reflected acoustic echo signals from moving objects within said structures;
   means for determining signals representing the difference between said transmitted and received signals;
   means for sampling the difference signals;
   means for determining the start and end of said patient's cardiac cycle in response to said patient's electrocardiogram signals;
   means responsive to the determined start and end of said patient's cardiac cycle and said sampled difference signals for dividing the latter into a predefined number of time segments of signals each representing the same amount of time with the total amount of time equal to one cardiac cycle;
   means for autoregressive spectrum analyzing said sampled difference signals to determine the power spectrum of said sampled difference signals of each of said time segments; and
   means responsive to the determined power spectrum of each of said time segments for displaying the blood velocity within said structures.

6. The system of claim 5 further comprising means for storing said determined power spectrum of said sampled difference signals of each of said time segments for a plurality of cardiac cycles;
   means for calculating the total energy of all the sampled difference signals of each particular time segment for said plurality of cardiac cycles;
   means for dividing the stored power spectrum by said total energy for each of said time segments to produce a normalized power spectrum; and
   means for averaging all normalized power spectra of individual time segments for said plurality of cardiac cycles.

7. The system of claim 6 further comprising means for displaying said averaged power spectrum for each time segment with different colors representing different power levels.

8. The system of claim 7 wherein said autoregressive spectrum analyzing means comprises means for performing linear predictive coding.

9. The system of claim 6 wherein said autoregressive spectrum analyzing means comprises:
means responsive to said sampled difference signals of each time segment for generating reflection coefficients for modeling the amount of object movement;
means responsive to said reflection coefficients and said sampled difference signals of each of said time segments for generating a residual energy level for each of said time segments representing energy not accounted for by said modeling; and
means responsive to said reflection coefficients and said residual energy level for each of said time segments for calculating said power spectrum of said sampled difference signals of each of said time segments.

10. A blood flow analysis system for measuring the velocity of blood moving within internal patient structures, comprising:
means for transmitting ultrasonic frequency acoustic signals into said patient structures for a plurality of cardiac cycles;
means for receiving the reflected acoustic echoed signals from moving acoustic scatterers in said blood over said plurality of cardiac cycles;
means for determining signals representing the difference between said transmitted and said received signals;
means for sampling the difference signals;
means for determining the start and end of each of said cardiac cycles in response to said patient's electrocardiogram signals;
means responsive to said start and end of each of said plurality of cardiac cycles and said corresponding sampled difference signals of each of said plurality of cardiac cycles for dividing said corresponding sampled difference signals into a predefined number of channels of said sampled difference signals for each of said plurality of cardiac cycles with each channel representing the same amount of time with the total amount of time of all channels of a particular cardiac cycle equal to that cardiac cycle;
means responsive to said sampled difference signals of each of said channels for generating reflection coefficients for modeling the amount of blood movement;
means responsive to said reflection coefficients and said sampled difference signals for each of said channels for generating a residual energy level for each of said channels representing energy not accounted for by said modeling;
means responsive to said reflection coefficients and said residual energy level for each of said channels for calculating the power spectrum of said sampled difference signals for each of said channels;
means for adding together said resulting power spectra together for each particular channel of all of said cardiac cycles;
means for calculating the total energy of all sampled difference signals for each particular channel for all of said cardiac cycles;
means for dividing the added resulting power spectrum by said total energy for each of said channels to produce a normalized power spectrum for each channel; and
means for displaying said normalized power spectrum for each channel.

11. The system of claim 10 wherein said means for generating said reflection coefficients comprises:
means for computing a forward error signal for each of said sampled difference signals for each channel representing the difference between each of said sampled difference signals and the subsequent ones of said difference signals of the same channel;
means for calculating a backward error signal for each of said sampled difference signals of each channel representing the difference between each of said sampled difference signals and preceding sampled difference signals of the same channel; and
means for computing reflection coefficients in response to said backward and forward error signals for each of said channels.

12. A method for measuring blood flow within internal blood vessel within a patient by analyzing sampled Doppler shifted signals from moving blood cells within the vessel during a cardiac cycle and electrocardiogram signals received from said patient, comprising the steps of:
determining the start and end of said patient's cardiac cycle in response to said electrocardiogram signals;
dividing said sampled Doppler shifted signals into a predefined plurality of time channels corresponding to one cardiac cycle;
calculating reflection coefficients modeling said blood flow in response to said sampled Doppler shifted signals of each of said time channels;
generating a residual energy level for each of said time channels representing the energy not accounted for by said modeling in response to said sampled Doppler shifted signals and said reflection coefficients; and
calculating the power spectrum of said sampled Doppler shifted signals for each of said time channels in response to said residual energy and said reflection coefficients; and
determining blood velocity within said vessel which is indicative of blood flow in response to said calculated power spectrum for each of said time channels.

13. The method of claim 12 further comprising the steps of:
storing said calculated power spectrum of said sampled Doppler shifted signals of each time channel for a plurality of cardiac cycles;
calculating the total energy of all of the sampled Doppler shifted signals of each particular time channel for said plurality of cardiac cycles;
dividing the stored power spectrum by said total energy for each of said time channels to produce a normalized power spectrum; and
averaging all normalized power spectra of individual time channels for said plurality of said cardiac cycles.

14. The method of claim 13 further comprising the step of displaying said average power spectrum for each time channel with different colors representing different power levels.

15. A method for measuring blood flow within internal blood vessels within a patient by analyzing sampled reflected Doppler shifted signals from moving blood cells within the vessels for a plurality of cardiac cycles, comprising the steps of:

determining the start and end of each of said cardiac cycles in response to said patient's electrocardiogram signals;

dividing said corresponding sampled reflected Doppler shifted signals in response to said start and end of each of said plurality of cardiac cycles into a predefined plurality of channels of said sampled Doppler shifted signals for each of said plurality of cardiac cycles with each channel representing the same amount of time with the total amount of time of all channels of a particular cardiac cycle equal to that cardiac cycle;

generating reflection coefficients for modeling the amount of blood movement in response to said sampled Doppler shifted signals of each of said channels;

generating a residual energy level for each of said channels representing energy not accounted for by said modeling in response to said reflection coefficients and said sampled Doppler shifted signals for each of said channels;

calculating the power spectrum of said sampled Doppler shifted signals for each of channels in response to said reflection coefficients and said residual energy level for each of said channels;

adding together the resulting power spectra for each particular channel of all of said cardiac cycles;

calculating the total energy of all sampled Doppler shifted signals for each particular channel for all of said cardiac cycles;

dividing the added power spectrum by said total energy for each of said channels to produce a normalized power spectrum for each channel; and displaying said normalized power spectrum for each channel.

16. The method of claim 15 wherein said step of generating said reflection coefficients comprises the steps of:

computing a forward error signal for each of said sampled Doppler shifted signals for each channel representing the difference between each of said sampled reflected signals and the subsequent ones of said sampled shifted signals of the same channel;

calculating a backward error signal for each of said sampled Doppler shifted signals of each channel representing the difference between each of said shifted signals and preceding sampled shifted signals of the same channel; and computing reflection coefficients in response to said backward and forward error signals for each of said channels.

17. A blood flow analysis system for measuring velocity of blood moving within internal patient structures, comprising:

means for transmitting ultrasonic frequency acoustic signals into said patient structures;

means for receiving reflected acoustic echo signals from moving objects within said patient structures;

means for determining signals representing the difference between said transmitted and said received signals;

means for sampling the difference signals;

means responsive to said sampled difference signals for dividing said sampled difference signals into a predefined number of time segments of signals;

means for autoregressive spectrum analyzing each of said time segments of said sampled difference signals to determine the power spectrum of said sampled difference signals for each of said time segments; and means responsive to the determined power spectrum of each of said time segments for determining the blood velocity indicative of the amount of blood flow within said internal patient structures.

18. The system of claim 17 further comprising means for storing said determined power spectrum of said sampled difference signals of each of said time segments for a plurality of cardiac cycles:

means for calculating the total energy of all of the sampled difference signals of each particular time segment for said plurality of cardiac cycles;

means for dividing the stored power spectrum by said total energy for each of said segments to produce a normalized power spectrum; and means for averaging all normalized power spectra of individual time segments for said plurality of cardiac cycles.

19. The system of claim 18 further comprising means for displaying said average power spectrum for each time segment with different colors representing different power levels.

20. The system of claim 19 wherein said spectrum analyzing means comprises:

means responsive to said sampled difference signals of each of said time segments for calculating reflection coefficients modeling said blood flow;

means responsive to said sampled difference signals and said reflection coefficients for generating an residual energy level for each of said time segments representing the energy not accounted for by said modeling; and means responsive to said residual energy level and said reflection coefficients for each of said time segments for calculating the power spectrum of said sampled difference signals for each of said time segments.

21. A method for measuring blood flow velocity within internal blood vessels within a patient by analyzing sampled Doppler shifted signals from moving blood cells within the vessels comprising the steps of:

dividing said sampled Doppler shifted signals into a predefined plurality of time channels;

calculating reflection coefficients modeling said blood flow in response to said sampled Doppler shifted signals of each of said time channels;

generating a residual energy level for each of said time channels representing the energy not accounted for by said modeling in response to said sampled Doppler shifted signals and said reflection coefficients;

calculating the power spectrum of said sampled Doppler shifted signals for each of said time channels in response to said residual energy and said reflection coefficients; and determining blood velocity indicative of the amount of blood flow in response to said calculated power spectrum for each of said time channels.

22. The method of claim 21 further comprising the steps of:

storing said calculated power spectrum of said sampled Doppler shifted signals of each time channel for a plurality of cardiac cycles;

calculating the total energy of all of the sampled Doppler shifted signals of each particular time channel for said plurality of cardiac cycles;

dividing the stored power spectrum by said total energy for each of said time channels to produce a normalized power spectrum; and averaging all normalized power spectra of individual time channels for said plurality of said cardiac cycles.

23. The method of claim 22 further comprising the step of displaying said average power spectrum for each time channel with different colors representing different power levels.

* * * * *

UNITED STATES PATENT AND TRADEMARK OFFICE
CERTIFICATE OF CORRECTION

PATENT NO: 4,759,374
DATED: July 26, 1988
INVENTOR(s): Catherine M. P. Kierney and Gustavus H. Zimmerman, III It is certified that errors appear in the above-identified patent and that said Letters Patent is hereby corrected as shown below:

Column 13, line 38 "blood flows" should read "blood flow",

Column 16, line 27 after "channels" insert --with the total of said time channels--, Column 17, line 56, "reflected acoustic echo" should read "reflected acoustical echo".

Signed and Sealed this

Twenty-seventh Day of April, 1993

*Attest:*

MICHAEL K. KIRK

*Attesting Officer*   *Acting Commissioner of Patents and Trademarks*